United States Patent
Zhu et al.

(10) Patent No.: US 12,377,043 B2
(45) Date of Patent: Aug. 5, 2025

(54) *SOLANUM LYCOPERSICUM* SEED OIL FREEZE-DRIED POWDER WITH WHITENING EFFICACY, COMPOSITION, AND PREPARATION METHOD AND APPLICATION THEREOF

(71) Applicants: Beijing Yipintang Pharmaceutical Technology Co., Ltd., Beijing (CN); Shenzhen Porshealth Bioengineering Co., Ltd., Shenzhen (CN)

(72) Inventors: Yingkui Zhu, Beijing (CN); Guoxun Xiao, Shenzhen (CN); Silu Zhang, Shenzhen (CN); Shan Lu, Shenzhen (CN)

(73) Assignees: Beijing Yipintang Pharmaceutical Technology Co., Ltd., Beijing (CN); Shenzhen Porshealth Bioengineering Co., Ltd., Shenzhen (CN)

( * ) Notice: Subject to any disclaimer, the term of this patent is extended or adjusted under 35 U.S.C. 154(b) by 0 days.

(21) Appl. No.: 18/435,068

(22) Filed: Feb. 7, 2024

(65) Prior Publication Data
US 2024/0173247 A1    May 30, 2024

(30) Foreign Application Priority Data
May 6, 2023 (CN) .......................... 202310501837.3

(51) Int. Cl.
*A61K 8/9789* (2017.01)
*A61Q 19/02* (2006.01)

(52) U.S. Cl.
CPC ............ *A61K 8/9789* (2017.08); *A61Q 19/02* (2013.01); *A61K 2236/00* (2013.01); *A61K 2800/84* (2013.01)

(58) Field of Classification Search
None
See application file for complete search history.

(56) References Cited

U.S. PATENT DOCUMENTS

| | | |
|---|---|---|
| 2008/0003189 A1 | 1/2008 | Umishio et al. |
| 2010/0008879 A1 | 1/2010 | Umishio et al. |
| 2011/0286953 A1 | 11/2011 | Suzuki et al. |

FOREIGN PATENT DOCUMENTS

| | | | | |
|---|---|---|---|---|
| AU | 2007283133 A1 | * | 2/2009 | ........... A23K 20/179 |
| WO | WO-2008004206 A2 | * | 1/2008 | ............. A61K 31/07 |
| WO | WO-2016018315 A1 | * | 2/2016 | ............. A45D 34/04 |
| WO | WO-2017038951 A1 | * | 3/2017 | ............. A61K 31/19 |

OTHER PUBLICATIONS

CNIPA, Notification of First Office Action for Chinese application CN202310501837.3, Jun. 15, 2023.
CNIPA, Notification to grant patent right for Chinese application CN202310501837.3, Jul. 1, 2023.

* cited by examiner

*Primary Examiner* — David J Blanchard
*Assistant Examiner* — Sarah J Chickos
(74) *Attorney, Agent, or Firm* — Hemisphere Law, PLLC; Zhigang Ma

(57) ABSTRACT

The present invention provides a *Solanum lycopersicum* seed oil freeze-dried powder with whitening efficacy, a composition, and a preparation method and application thereof. The *Solanum lycopersicum* seed oil freeze-dried powder has significant whitening efficacy. If the *Solanum lycopersicum* seed oil freeze-dried powder is used in combination with a lemon verbena extract with a dose ratio of 3:1, the whitening effect is synergistic with the lemon verbena extract. The *Solanum lycopersicum* seed oil freeze-dried powder is an ideal raw material for preparing a whitening drug and a cosmetic.

4 Claims, 3 Drawing Sheets

SOLANUM LYCOPERSICUM SEED OIL FREEZE-DRIED POWDER WITH WHITENING EFFICACY, COMPOSITION, AND PREPARATION METHOD AND APPLICATION THEREOF

TECHNICAL FIELD

The present invention belongs to the field of biomedical technologies, and particularly relates to a *Solanum lycopersicum* seed oil freeze-dried powder with whitening efficacy, a composition, and a preparation method and application thereof.

BACKGROUND

All people search for beauty. With the rapid development of society, people have been more and more in favor of white skin, and their requirements for whitening efficacy of drugs or cosmetics have been gradually increased. At present, more and more scientific researchers have tended to find safe and efficient whitening active substances from natural plants.

*Solanum lycopersicum* is an annual or perennial herbaceous plant from Lycopersicon of Solanaceae. Its seeds are yellowish, and its flowering and fruiting period is in the autumn and the winter. As an infinite-growth-type tomato, the *Solanum lycopersicum* has a single fruit weight of 150-200 g. Mature *Solanum lycopersicum* turns to gold, has bright appearance, good quality and high fruit firmness, and can be stored for a long time. The *Solanum lycopersicum* tastes sweet and sour, and is slightly cold. The *Solanum lycopersicum* contains various vitamins, and further contains unique more hydrogen lycopene (lycopene, phytofluene and phytoene) that other categories of tomatoes do not have. As a natural raw material that protects, moistens and maintains the skin etc., it has a nourishing effect on skin, can also balance production of free radicals and can promote generation of collagen.

Lemon verbena (Latin name: *Aloysia citrodora*) is a plant native to South America, introduced into China. It is often used for food flavoring, and for tea drinking in France; and its leaves are for medicinal purposes. The lemon verbena has the efficacy of treating a palpitation, an anxiety, insomnia, asthma, a cold, etc.

However, there is no report on the use of *Solanum lycopersicum* seed oil freeze-dried powder and a lemon verbena extract for whitening in the prior art. Therefore, it is necessary to develop a novel *Solanum lycopersicum* seed oil freeze-dried powder with whitening efficacy and a composition thereof.

SUMMARY

A purpose of the present invention is to provide a *Solanum lycopersicum* seed oil freeze-dried powder with outstanding whitening efficacy, a composition, and a preparation method and application thereof.

In order to achieve the above inventive purpose, the present invention adopts the following technical solution:

In a first aspect, the present invention provides a *Solanum lycopersicum* seed oil freeze-dried powder with whitening efficacy. In the freeze-dried powder, a content of phytoene is 25-40%, and a content of phytofluene is 8-12%.

Preferably, the content of the phytoene is 29-35%, and the content of the phytofluene is 10-11%.

More preferably, the content of the phytoene is 33.6%, and the content of the phytofluene is 10.2%.

The present invention further provides a preparation method for *Solanum lycopersicum* seed oil freeze-dried powder, including the following steps:

S1. cleaning, naturally drying and crushing *Solanum lycopersicum*, and picking out *Solanum lycopersicum* seeds;

S2. crushing the above *Solanum lycopersicum* seeds into 20-80 meshes, performing extraction on the crushed *Solanum lycopersicum* seeds by using a supercritical carbon dioxide extraction technology, and performing separation to obtain *Solanum lycopersicum* seed oil, wherein an extraction temperature is 40-60° C., an extraction time is 1-5 h, and an extraction pressure is 20-50 MPa;

S3. including the above *Solanum lycopersicum* seed oil by hydroxypropyl cyclodextrin to obtain a *Solanum lycopersicum* seed oil inclusion complex, and preparing the *Solanum lycopersicum* seed oil inclusion complex into freeze-dried powder by using a vacuum freeze-drying technology to obtain the *Solanum lycopersicum* seed oil freeze-dried powder.

Preferably, the extraction temperature is 45° C., the extraction time is 2.5 h, and the extraction pressure is 40 MPa.

In a second aspect, the present invention provides a composition with the whitening efficacy, including the following raw materials: 1-5 parts of *Solanum lycopersicum* seed oil freeze-dried powder, and 0.5-3 parts of lemon verbena extract, Preferably, 3 parts of the *Solanum lycopersicum* seed oil freeze-dried powder, and 1 part of the lemon verbena extract.

The present invention further provides a preparation method for lemon verbena extract freeze-dried powder, including the following steps: crushing and drying lemon verbena, adding 3 times of 80% ethanol solution, heating a mixture for extraction for 0.5-2 h, and filtering, concentrating and freeze-drying a resultant to obtain the lemon verbena extract freeze-dried powder.

In a third aspect, the present invention provides a drug or a cosmetic with whitening efficacy. Its active component is prepared by adding a carrier that is commonly used in pharmaceutics to the *Solanum lycopersicum* seed oil freeze-dried powder or the composition of the present invention.

In a fourth aspect, the present invention provides an application of the *Solanum lycopersicum* seed oil freeze-dried powder or the composition in preparation of a drug or a cosmetic with whitening efficacy.

The present invention has the beneficial effects:

(1) When used alone, the *Solanum lycopersicum* seed oil freeze-dried powder extracted by the present invention has no toxic effect on mouse B16 melanoma cells, and obviously inhibits melanin synthesis and the intracellular tyrosinase activity in the mouse B16 melanoma cells and the mushroom tyrosinase activity in vitro. It shows that the *Solanum lycopersicum* seed oil freeze-dried powder extracted by the present invention has the significant whitening effect.

(2) The lemon verbena extract is used in combination with the *Solanum lycopersicum* seed oil freeze-dried powder extracted by the present invention. The lemon verbena extract can obviously improve the inhibition effects of the *Solanum lycopersicum* seed oil freeze-dried powder on melanin synthesis and the intracellular tyrosinase activity in the mouse B16 melanoma cells and the mushroom tyrosinase activity in vitro; and in a case of the dose ratio of 3:1, after combined use of the above two, they have the synergistic whitening effect.

DETAILED DESCRIPTION

Figure 1:
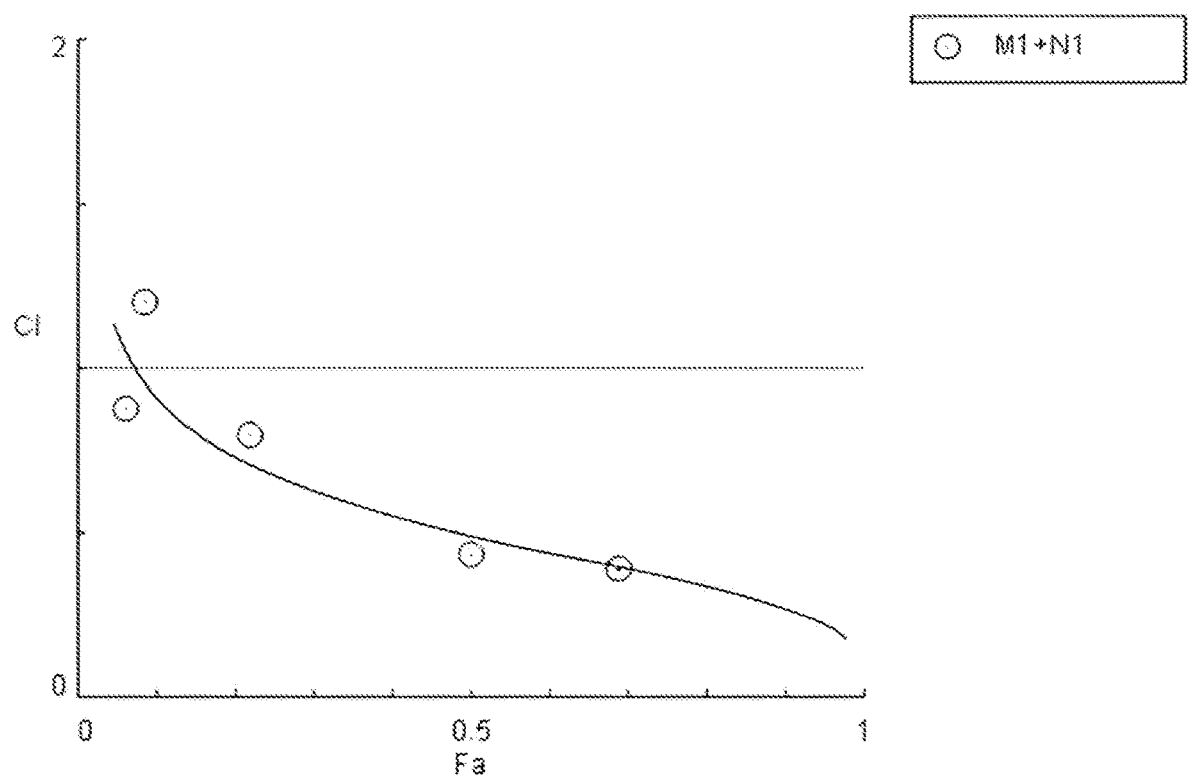
FIG. 1 is a Fa-CI diagram of a composition for inhibiting melanin synthesis in mouse B16 melanoma cells.

For better understanding the present invention, the implementations of the present invention are described in detail below in combination with the embodiments. However, those skilled in the art should understand that the following embodiments are only used for describing the present invention, and should not be taken as limiting the scope of the present invention.

Embodiment 1: Preparation of *Solanum lycopersicum* Seed Oil Freeze-Dried Powder S1. cleaning, naturally drying and crushing *Solanum lycopersicum*, and picking out *Solanum lycopersicum* seeds;

S2. crushing the above *Solanum lycopersicum* seeds into 20 meshes, performing extraction on the crushed *Solanum lycopersicum* seeds by using a supercritical carbon dioxide extraction technology, and performing separation to obtain *Solanum lycopersicum* seed oil, wherein an extraction temperature is 50° C., an extraction time is 4 h, and an extraction pressure is 25 MPa;

S3. including the above *Solanum lycopersicum* seed oil by hydroxypropyl cyclodextrin to obtain a *Solanum lycopersicum* seed oil inclusion complex, and preparing the *Solanum lycopersicum* seed oil inclusion complex into freeze-dried powder by using a vacuum freeze-drying technology to obtain the *Solanum lycopersicum* seed oil freeze-dried powder.

Through determination, in the prepared *Solanum lycopersicum* seed oil freeze-dried powder, a content of phytoene is 27.3%, and a content of phytofluene is 8.1%.

Embodiment 2: Preparation of *Solanum lycopersicum* Seed Oil Freeze-Dried Powder S1. cleaning, naturally drying and crushing *Solanum lycopersicum*, and picking out *Solanum lycopersicum* seeds;

S2. crushing the above *Solanum lycopersicum* seeds into 40 meshes, performing extraction on the crushed *Solanum lycopersicum* seeds by using a supercritical carbon dioxide extraction technology, and performing separation to obtain *Solanum lycopersicum* seed oil, wherein an extraction temperature is 60° C., an extraction time is 5 h, and an extraction pressure is 20 MPa;

S3. including the above *Solanum lycopersicum* seed oil by hydroxypropyl cyclodextrin to obtain a *Solanum lycopersicum* seed oil inclusion complex, and preparing the *Solanum lycopersicum* seed oil inclusion complex into freeze-dried powder by using a vacuum freeze-drying technology to obtain the *Solanum lycopersicum* seed oil freeze-dried powder.

Through determination, in the prepared *Solanum lycopersicum* seed oil freeze-dried powder, a content of phytoene is 30.2%, and a content of phytofluene is 8.7%.

Embodiment 3: Preparation of *Solanum lycopersicum* Seed Oil Freeze-Dried Powder S1. cleaning, naturally drying and crushing *Solanum lycopersicum*, and picking out *Solanum lycopersicum* seeds;

S2. crushing the above *Solanum lycopersicum* seeds into 60 meshes, performing extraction on the crushed *Solanum lycopersicum* seeds by using a supercritical carbon dioxide extraction technology, and performing separation to obtain *Solanum lycopersicum* seed oil, wherein an extraction temperature is 45° C., an extraction time is 2.5 h, and an extraction pressure is 40 MPa;

S3. including the above *Solanum lycopersicum* seed oil by hydroxypropyl cyclodextrin to obtain a *Solanum lycopersicum* seed oil inclusion complex, and preparing the *Solanum lycopersicum* seed oil inclusion complex into freeze-dried powder by using a vacuum freeze-drying technology to obtain the *Solanum lycopersicum* seed oil freeze-dried powder.

Through determination, in the prepared *Solanum lycopersicum* seed oil freeze-dried powder, a content of phytoene is 33.6%, and a content of phytofluene is 10.2%.

Embodiment 4: Preparation of Composition with Whitening Efficacy

The composition includes the following raw materials: 3 parts of *Solanum lycopersicum* seed oil freeze-dried powder, and 1 part of the lemon verbena extract, wherein a preparation method for the lemon verbena extract includes the following steps: crushing and drying lemon verbena; adding 3 times of 80% ethanol solution; heating a mixture for extraction for 0.5-2 h; filtering and concentrating a resultant to a volume of 100 ml; and performing freeze-drying to obtain the lemon verbena extract. The *Solanum lycopersicum* seed oil freeze-dried powder is the freeze-dried powder prepared in embodiment 3.

In order to better illustrate the technical effects of the present invention, the following experiments are performed.

Experimental Example 1: Detection on Inhibition Against B16 Cells with MTT Method Sample preparation: 5, 10, 20, 40 and 80 mg of the *Solanum lycopersicum* seed oil freeze-dried powder prepared in embodiment 3 were dissolved into 1000 ml of 1640 complete medium to prepare sample solutions with gradient concentrations of 5, 10, 20, 40 and 80 mg/L (hereinafter referred to as an M1 group). 1, 2, 4, 8 and 16 mg of the lemon verbena extract prepared in embodiment 4 were dissolved into 1000 ml of 1640 complete medium to prepare sample solutions with gradient concentrations of 1, 2, 4, 8 and 16 mg/L (hereinafter referred to as an N1 group). In addition, the *Solanum lycopersicum* seed oil freeze-dried powder and the lemon verbena extract prepared in embodiment 3 and embodiment 4 were proportioned by a mass ratio of 3:1, that is, 1.5+0.5, 3+1, 6+2, 12+4 and 24+8 mg of the *Solanum lycopersicum* seed oil freeze-dried powder plus the lemon verbena extract were weighed to be dissolved into 1000 ml of 1640 complete medium respectively, to prepare 1.5+0.5, 3+1, 6+2, 12+4 and 24+8 mg/L of the composition sample solutions (hereinafter referred to as an M1+N1 group). All the samples were filtered with a 0.22 μm sterile filter head for later use.

Mouse B16 melanoma cells in a logarithmic growth phase were selected and digested with 0.25% trypsin solution; a resultant was prepared into a cell suspension with a density of 1× $10^5$ cells/mL by using the 1640 complete medium; and the cell suspension was inoculated to a 96-well culture plate with 100 μL per well, and cultured in a 5% $CO_2$ incubator at 37° C. After 24 h of adherence, the cells were divided into three groups, and the above PBS sample solutions containing different mass concentrations of the samples were added respectively. An equal volume of cell suspension was added to a control group; and a blank group was also set with an equal volume of 1640 complete medium added with 100 μL per well. Three replicates were set for each mass concentration, and cultured in a 5% $CO_2$ incubator at 37° C. for 72 h. An absorbance was measured at 570 nm by the MTT method. A relative cell proliferation rate was calculated according to the following formula: relative cell proliferation rate=(A−C)/(B−C)×100%. In the formula, A is an average absorbance of a sample group; B is an average absorbance of the control group; and C is an average absorbance of the control group. Results are shown in Table 1.

TABLE 1

Effect on Viability of B16 Cells

| Drug | Concentration (mg/L) | Inhibition rate/% |
|---|---|---|
| M1 | 5 | 1.6 ± 1.0 |
|  | 10 | 2.1 ± 0.3 |
|  | 20 | 3.1 ± 0.4 |
|  | 40 | 3.9 ± 0.4 |
|  | 80 | 4.3 ± 0.8 |
| N1 | 1 | 1.3 ± 0.2 |
|  | 2 | 1.6 ± 0.4 |
|  | 4 | 2.8 ± 0.3 |
|  | 8 | 2.5 ± 0.1 |
|  | 16 | 2.8 ± 0.3 |
| M1 + N1 | 1.5 + 0.5 | 2.0 ± 0.7 |
|  | 3 + 1 | 3.2 ± 0.2 |
|  | 6 + 2 | 3.0 ± 0.4 |
|  | 12 + 4 | 3.6 ± 0.5 |
|  | 24 + 8 | 5.0 ± 0.2 |

Note:
Data are expressed as mean ± standard deviation.
Similarly hereinafter.

Thus, in a case that the *Solanum lycopersicum* seed oil freeze-dried powder solution and the lemon verbena extract have the highest mass concentrations of 80 mg/L and 16 mg/L, and are used in combination, their inhibition rate against the B16 cells is 5% or below, and the cell morphologies are normal. It shows that the *Solanum lycopersicum* seed oil freeze-dried powder and the lemon verbena extract have no toxic effect on cells.

Experimental Example 2: Determination on Content of Melanin in B16 Cells

Preparation of the samples are the same as that in experimental example 1. The cultured third generation of B16 cells were inoculated to a 6-well plate at a density of 1× $10^4$ cells/mL, and a fluid was changed after 24 h. Media containing different mass concentrations of the above samples were added, and three replicates were set for each mass concentration. The control group used the 1640 complete medium instead of the sample solutions. After incubation at 37° C. and 5% $CO_2$ for 72 h, a supernatant was discarded. 1 mL of trypsin solution with a mass concentration of 2.5 g/L was added to each well for digestion for 5 min at a room temperature. 4 mL of the 1640 complete medium was added to stop digestion, and a resultant was blown into a single cell suspension. 0.5 mL of the single cell suspension was taken for cell counting; the other cell suspension was centrifuged for 10 min; a supernatant was discarded; 1 mL of 1 mol/L NaOH solution was added; a mixture was incubated in a water bath at 90° C. for 2 h; and an absorbance was measured at 490 nm on a microplate reader. The inhibition rate of the sample against melanin synthesis was calculated according to the following formula: inhibition rate=(1− (absorbance of sample well/cell density of sample well)÷ (absorbance of control well/cell density of control well)× 100%). Results are shown in Table 2. CompuSyn software was used to calculate a combination index (i.e. CI value) of combined use of the *Solanum lycopersicum* seed oil freeze-dried powder and the lemon verbena extract. Results are shown in FIG. 1.

TABLE 2

Effect on Melanin Synthesis in B16 Cells

| Drug | Concentration (mg/L) | Inhibition rate/% |
|---|---|---|
| M1 | 5 | 10.5 ± 0.8 |
|  | 10 | 21.7 ± 1.3 |
|  | 20 | 40.4 ± 2.0 |
|  | 40 | 53.2 ± 2.5 |
|  | 80 | 66.9 ± 2.4 |
| N1 | 1 | 3.3 ± 0.6 |
|  | 2 | 7.3 ± 0.9 |
|  | 4 | 12.2 ± 1.3 |
|  | 8 | 19.8 ± 1.3 |
|  | 16 | 30.7 ± 1.4 |
| M1 + N1 | 1.5 + 0.5 | 6.1 ± 0.3 |
|  | 3 + 1 | 8.6 ± 1.1 |
|  | 6 + 2 | 21.9 ± 1.5 |
|  | 12 + 4 | 50.3 ± 1.7 |
|  | 24 + 8 | 68.9 ± 1.8 |

It can be seen therefrom, after the B16 cells are treated with the *Solanum lycopersicum* seed oil freeze-dried powder solution, the inhibition rate against melanin synthesis in the B16 cells is highest at (66.9±2.4)%, and the *Solanum lycopersicum* seed oil freeze-dried powder solution shows a significant inhibition ability against melanin synthesis and is mass concentration dependent. After addition of the lemon verbena extract, the inhibition ability of the *Solanum lycopersicum* seed oil freeze-dried powder solution against melanin synthesis may be improved; and in combination with that the CI value <1 after the inhibition rate of combined use of the *Solanum lycopersicum* seed oil freeze-dried powder and the lemon verbena extract reaches 20% or above in FIG. 1, it shows that if the *Solanum lycopersicum* seed oil freeze-dried powder and the lemon verbena extract are used in combination with a dose ratio of 3:1, their inhibition against melanin synthesis in the B16 cells is synergistic.

Experimental Example 3: Determination on Tyrosinase Activity in B16 Cells

Figure 2:
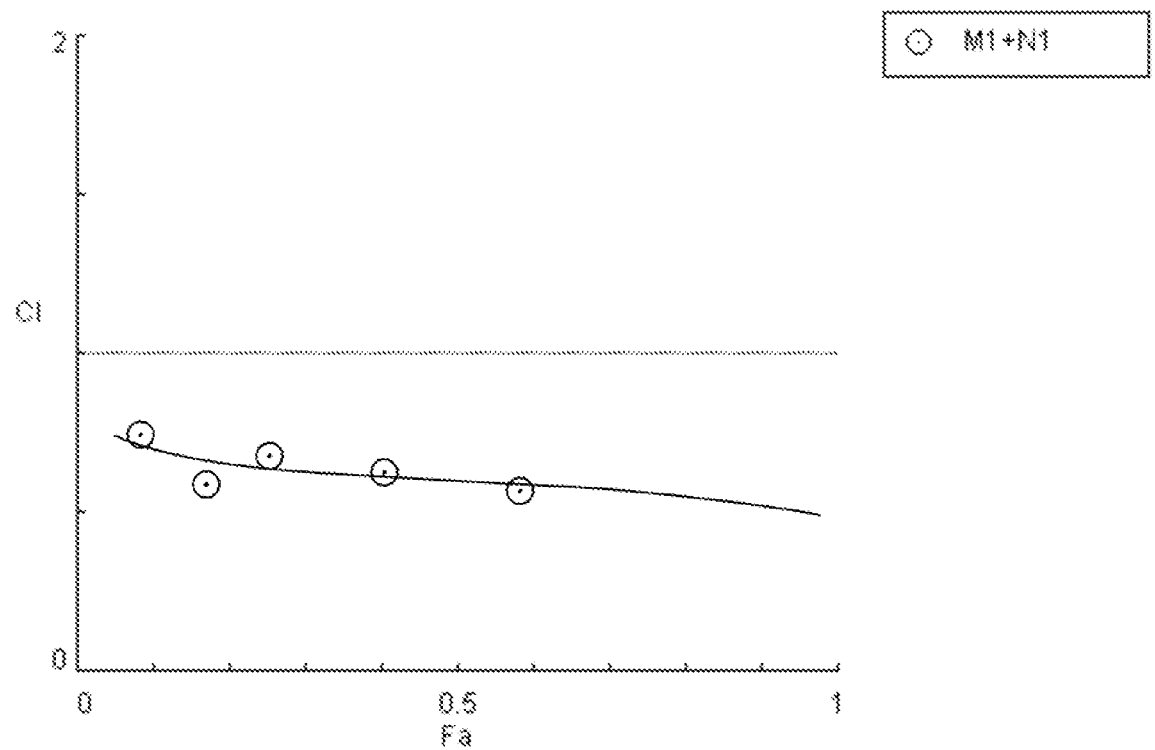
FIG. 2 is a Fa-CI diagram of a composition for inhibiting the tyrosinase activity in mouse B16 melanoma cells.

Preparation of the samples are the same as that in experimental example 1. Culture was performed on a 96-well plate with an amount of B16 single cell suspension added being (7-8)× $10^3$ cells/well. After 24 h of adherence, media containing different mass concentrations of the above samples were added, and three replicates were set for each mass concentration. The control group used the 1640 complete medium instead of the sample solutions. After incubation at 37° C. and 5% $CO_2$ for 72 h, a supernatant was discarded. The cells were washed twice with PBS (pH =7.4), and 50 μL of 1% octylphenol polyoxyethylene ether (Triton X-100) solution was added to each well. The cells were quickly frozen at −80° C. for 30 min, and then melted at the room temperature to make them completely ruptured. After pre-warming at 37° C. for 5 min, 10 μL of 1% L-DOPA solution was added for a reaction at 37° C. for 2 h. An absorbance was measured at 490 nm on a microplate reader. The inhibition rate against the tyrosinase activity was calculated according to the following formula: inhibition rate=(1−average absorbance of sample group/average absorbance of control group)×100%. Results are shown in Table 3. Ditto, CompuSyn software was used to calculate the combination index. Results are shown in FIG. 2.

TABLE 3

Effect on Tyrosinase Activity in B16 Cells

| Drug | Concentration (mg/L) | Inhibition rate/% |
|---|---|---|
| M1 | 5 | 9.4 ± 1.0 |
|  | 10 | 18.3 ± 0.8 |
|  | 20 | 32.9 ± 2.4 |
|  | 40 | 46.8 ± 1.4 |
|  | 80 | 59.9 ± 2.2 |
| N1 | 1 | 6.7 ± 1.1 |
|  | 2 | 10.5 ± 1.2 |
|  | 4 | 18.6 ± 1.2 |
|  | 8 | 28.7 ± 1.8 |
|  | 16 | 40.2 ± 1.2 |
| M1 + N1 | 1.5 + 0.5 | 8.3 ± 0.8 |
|  | 3 + 1 | 17.2 ± 1.4 |
|  | 6 + 2 | 25.4 ± 1.6 |
|  | 12 + 4 | 40.5 ± 1.1 |
|  | 24 + 8 | 58.3 ± 1.9 |

It can be seen therefrom, after the B16 cells are treated with the *Solanum lycopersicum* seed oil freeze-dried powder solution, the inhibition rate against the tyrosinase activity in the B16 cells is highest at (59.9 ±2.2)%, and the *Solanum lycopersicum* seed oil freeze-dried powder solution shows a significant inhibition effect on the intracellular tyrosinase activity and is mass concentration dependent. After addition of the lemon verbena extract, the inhibition effect of the *Solanum lycopersicum* seed oil freeze-dried powder solution on the intracellular tyrosinase activity may be improved; and in combination with that the CI value <1 after combined use of the *Solanum lycopersicum* seed oil freeze-dried powder and the lemon verbena extract in FIG. 2, it shows that if the *Solanum lycopersicum* seed oil freeze-dried powder and the lemon verbena extract are used in combination with a dose ratio of 3:1, their inhibition against the tyrosinase activity in the B16 cells is synergistic.

Experimental Example 4: Determination on Mushroom Tyrosinase Activity In Vitro

Sample preparation: 5, 10, 20, 40 and 80 mg of the *Solanum lycopersicum* seed oil freeze-dried powder prepared in embodiment 3 were dissolved into 1000 ml of a PBS solution to prepare sample solutions with gradient concentrations of 5, 10, 20, 40 and 80 mg/L (hereinafter referred to as an M group). 1, 2, 4, 8 and 16 mg of the lemon verbena extract prepared in embodiment 4 were dissolved into 1000 ml of the PBS solution to prepare sample solutions with gradient concentrations of 1, 2, 4, 8 and 16 mg/L (hereinafter referred to as an N group). In addition, the *Solanum lycopersicum* seed oil freeze-dried powder and the lemon verbena extract prepared in embodiment 3 and embodiment 4 were proportioned by a mass ratio of 3:1, that is, 1.5+0.5, 3+1, 6+2, 12+4 and 24+8 mg of the *Solanum lycopersicum* seed oil freeze-dried powder plus the lemon verbena extract were weighed to be dissolved into 1000 ml of the PBS solution respectively, to prepare 1.5+0.5, 3+1, 6+2, 12+4 and 24+8 mg/L of composition sample solutions (hereinafter referred to as an M+N group). All the samples were filtered with a 0.22 μm sterile filter head for later use.

Figure 3:
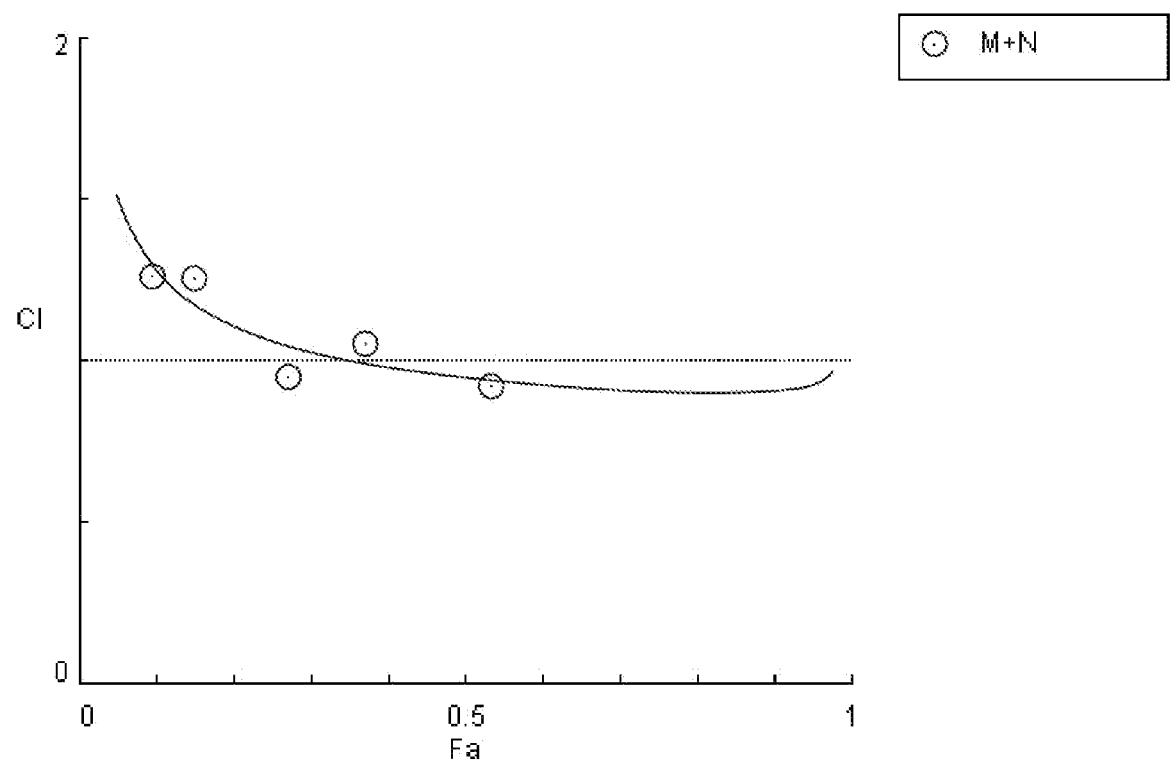
FIG. 3 is a Fa-CI diagram of a composition for inhibiting the mushroom tyrosinase activity in vitro.

According to an experimental method for inhibiting tyrosinase in vitro in the literature (Ma Jingbo, *Research on Biological Effects of Salidroside on Melanocytes and Discussion on Some Issues in Whitening Chinese Herbal Medicine Screening Process* [D]. Fudan University, 2003) and its improvement: 2 mL of the above PBS sample solutions containing different mass concentrations of samples were taken, and the control group used the PBS solution instead; mixed solutions of them and tyrosinase (100 U) were incubated at 37° C. for 10 min; 1 mL of 0.003 mol/L dopa reaction solution was added for continued incubation at 37° C. for 2 min; and an absorbance was measured at 475 nm immediately. The inhibition rate against the tyrosinase activity was calculated according to the following formula: inhibition rate=((A−B)−(C−D))/(A−B)×100%. In the formula, A is an absorbance, measured at 475 nm, of a mixture without a sample and with tyrosinase; B is an absorbance, measured at 475 nm, of a mixture without the sample and the tyrosinase; C is an absorbance, measured at 475 nm, of a mixture with the sample and the tyrosinase; and D is an absorbance, measured at 475 nm, of a mixture with the sample and without the tyrosinase. Results are shown in Table 4. Ditto, CompuSyn software was used to calculate the combination index. Results are shown in FIG. 3.

TABLE 4

Effect on Activity of Extracellular Tyrosinase

| Drug | Concentration (mg/L) | Inhibition rate/% |
|---|---|---|
| M | 5 | 15.3 ± 1.6 |
|  | 10 | 22.3 ± 2.0 |
|  | 20 | 36.7 ± 1.1 |
|  | 40 | 51.4 ± 1.9 |
|  | 80 | 71.4 ± 1.1 |
| N | 1 | 12.1 ± 1.7 |
|  | 2 | 18.8 ± 0.6 |
|  | 4 | 24.4 ± 0.7 |
|  | 8 | 37.7 ± 1.5 |
|  | 16 | 44.7 ± 1.8 |
| M + N | 1.5 + 0.5 | 9.5 ± 0.8 |
|  | 3 + 1 | 15.0 ± 1.3 |
|  | 6 + 2 | 27.1 ± 1.5 |
|  | 12 + 4 | 37.1 ± 2.0 |
|  | 24 + 8 | 53.4 ± 1.9 |

It can be seen therefrom, after treatment with the *Solanum lycopersicum* seed oil freeze-dried powder solution, the inhibition rate against the activity of tyrosinase in vitro is highest at (71.4±1.1)%, and the *Solanum lycopersicum* seed oil freeze-dried powder solution shows a significant inhibition effect on the tyrosinase activity and is mass concentration dependent. After addition of the lemon verbena extract, the inhibition effect of the *Solanum lycopersicum* seed oil freeze-dried powder solution on the activity of the tyrosinase in vitro may be improved; and in combination with that the CI value <1 after the inhibition rate of combined use of the *Solanum lycopersicum* seed oil freeze-dried powder and the lemon verbena extract reaches 50% or above in FIG. 3, it shows that if the *Solanum lycopersicum* seed oil freeze-dried powder and the lemon verbena extract are used in combination with a dose ratio of 3:1, their inhibition against the activity of the tyrosinase in vitro is synergistic.

In conclusion, according to the experimental results of the present invention, it can be known that when used alone, the *Solanum lycopersicum* seed oil freeze-dried powder has no toxic effect on the cells, and has the effects of inhibiting melanin generation and the tyrosinase activity in the mouse B16 melanoma cells and the mushroom tyrosinase activity in vitro. It shows that the *Solanum lycopersicum* seed oil freeze-dried powder has the significant whitening effect; and in a case of combined use of the *Solanum lycopersicum* seed oil freeze-dried powder and the lemon verbena extract, the whitening effect may be improved, and they have the synergistic effect. Therefore, the *Solanum lycopersicum* seed oil freeze-dried powder and the composition thereof of the present invention may serve as a novel drug or cosmetic for whitening.

The applicant declares that the present invention describes *Solanum lycopersicum* seed oil freeze-dried powder with the whitening efficacy, a composition, and a preparation method and application thereof of the present invention through the above embodiments, but the present invention is not limited to the above embodiments, that is, it does not mean that the present invention must be implemented relying on the above embodiments. Those skilled in the art should understand that any improvement on the present invention, equivalent replacements of various raw materials of the product of the present invention, addition of auxiliary components, selection of specific methods, etc., all fall within the protection scope and disclosure scope of the present invention.

The above describes the preferred implementation of the present invention in detail. However, the present invention is not limited to the specific details of the above implementations. Within the scope of the technical conception of the present invention, various simple variations on the technical solutions of the present invention can be made, and belong to the protection scope of the present invention.

In addition, it should be noted that the specific technical features described in the above specific implementations can be combined in any appropriate way without contradiction. In order to avoid unnecessary repetition, the present invention will not describe various possible combination modes separately.

What is claimed is:

1. A composition of *Solanum lycopersicum* seed oil freeze-dried powder with whitening efficacy, comprising the following raw materials: *Solanum lycopersicum* seed oil freeze-dried powder and lemon *verbena* extract freeze-dried powder, wherein a mass ratio of the lemon *verbena* extract freeze-dried powder to the *Solanum lycopersicum* seed oil freeze-dried powder is 4:12 (mg/L), and in the *Solanum lycopersicum* seed oil freeze-dried powder, a weight percent of phytoene is 33.6%, and a weight percent of phytofluene is 10.2%.

2. A drug with whitening efficacy, prepared by adding a carrier that is commonly used in pharmaceutics to the composition of *Solanum lycopersicum* seed oil freeze-dried powder according to claim 1.

3. A skin care product with whitening efficacy, prepared by adding a solvent to the composition of *Solanum lycopersicum* seed oil freeze-dried powder according to claim 1.

4. A method of preparing a drug or a cosmetic with whitening efficacy, comprising:
    providing a composition of *Solanum lycopersicum* seed oil freeze-dried powder, wherein providing the composition of *Solanum lycopersicum* seed oil freeze-dried powder comprises:
        cleaning, drying and crushing *Solanum lycopersicum*, and picking out *Solanum lycopersicum* seeds;
        crushing the *Solanum lycopersicum* seeds into 20 meshes, performing extraction on the crushed *Solanum lycopersicum* seeds by using a supercritical carbon dioxide extraction technology, and performing separation to obtain *Solanum lycopersicum* seed oil, wherein an extraction temperature is 50° C., an extraction time is 4 h, and an extraction pressure is 25 MPa; and
    including the *Solanum lycopersicum* seed oil by hydroxypropyl cyclodextrin to obtain a *Solanum lycopersicum* seed oil inclusion complex, and preparing the *Solanum lycopersicum* seed oil inclusion complex into freeze-dried powder by using a vacuum freeze-drying technology to obtain the *Solanum lycopersicum* seed oil freeze-dried powder;
    crushing and drying lemon *verbena*; adding 3 times of 80% ethanol solution with the lemon *verbena* to obtain a mixture; heating the mixture for extraction for 0.5-2 h; filtering and concentrating the heated mixture to a volume of 100 ml; and performing freeze-drying to obtain lemon *verbena* extract freeze-dried powder; and
    mixing the lemon *verbena* extract freeze-dried powder and the *Solanum lycopersicum* seed oil freeze-dried powder, a mass ratio of the lemon *verbena* extract freeze-dried powder to the *Solanum lycopersicum* seed oil freeze-dried powder is 4:12 (mg/L).

* * * * *